R. B. WHITMARSH.

WATER BAG.

APPLICATION FILED APR. 22, 1915.

Reissued Nov. 30, 1915.

14,024.

Witnesses,
Alfred H. Daehler
A. Gearing.

Inventor,
Robert. B. Whitmarsh,
By Raymond Ford Schulz
His Attorney.

UNITED STATES PATENT OFFICE.

ROBERT B. WHITMARSH, OF LOS ANGELES, CALIFORNIA.

WATER-BAG.

14,024. Specification of Reissued Letters Patent. Reissued Nov. 30, 1915.

Original No. 1,126,601, dated January 26, 1915, Serial No. 743,707. Application for reissue filed April 22, 1915. Serial No. 23,254.

*To all whom it may concern:*

Be it known that I, ROBERT B. WHITMARSH, a subject of the King of England, residing at Los Angeles, in the county of Los Angeles and State of California, have invented new and useful Improvements in Water-Bags, of which the following is a specification.

Water-bags as now constructed do not conform to the outlines of the face and are therefore not adapted to produce the best results when used for facial treatment.

It is the object of my invention to provide a water-bag which will conform to the outlines of the face and at the same time will permit the person on whom it is being used to breathe freely.

Figure 1:
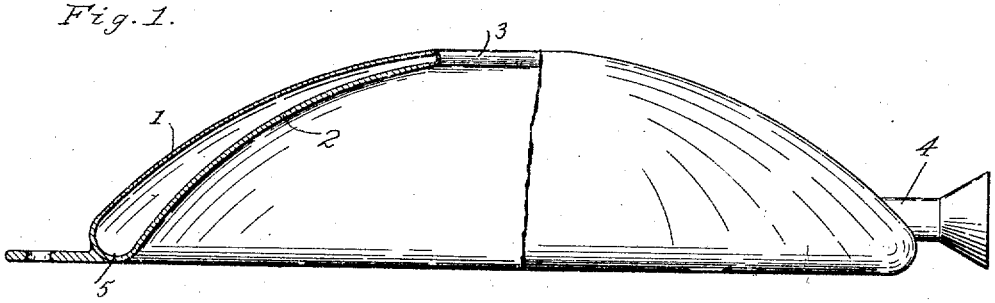
Figure 2:
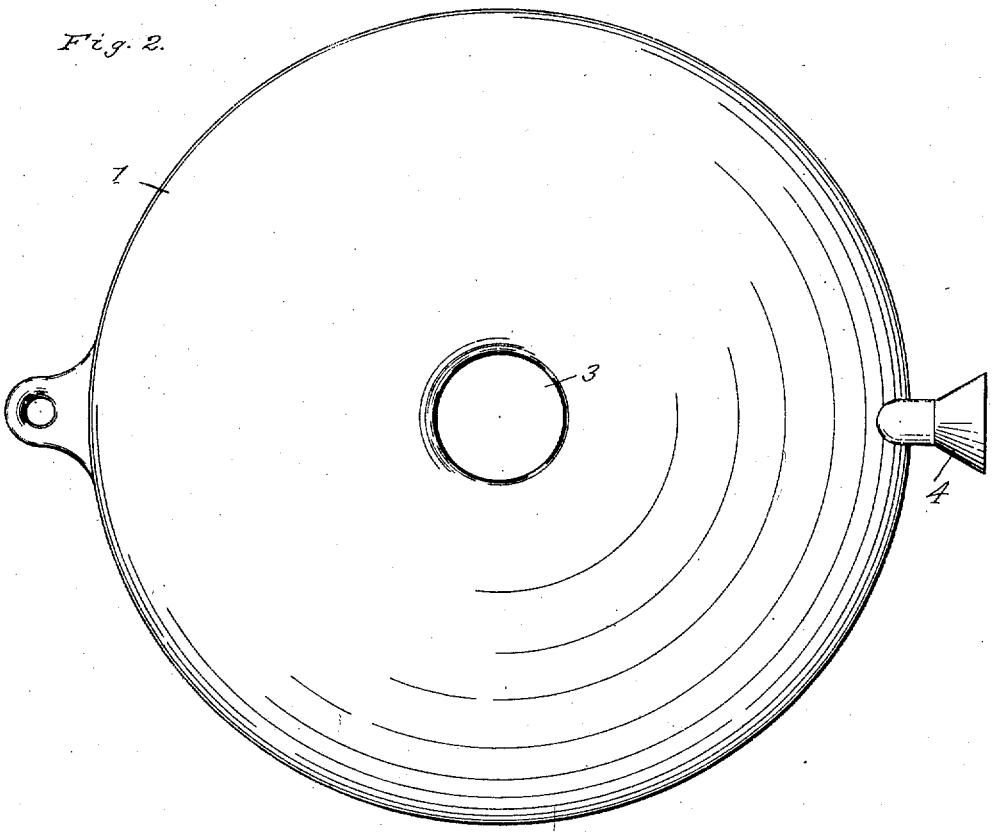

In the drawings forming a part hereof: Figure 1 is a side elevation, partly in section, of my improved water-bag. Fig. 2 is a top plan.

The walls 1 and 2 of my water-bag are in shape the same as the segment of the walls of a hollow globe. Wall 1 is the segment of a globe of a little greater diameter than that of wall 2. These walls are connected together at the center and a central aperture 3 cut out so as to form an aperture through which the person on whom it is used may breathe freely. The bottom portions or outer edges of the walls are connected by a curved circular bottom piece 5. A filling nozzle 4 of ordinary construction is provided.

In using the bag, after it is filled about one-third to one-half full, it is laid on the face of the person on whom it is used after such person has placed himself or herself in a recumbent position with face up. The central aperture is placed so that the air will freely flow therethrough to the nose of the person on whom it is being used. The walls are made of any suitable flexible water proof material.

By making the walls in shape the segment of a hollow globe, when partially or wholly filled the bag will conform to the face. If hot water is used the bag is only partially filled as the steam will rise to the top portion. A bag of this form is also more useful for application to other parts as it will fit closer to the body than a bag with parallel or flat walls. It will be manifest that if the bag is wholly or sufficiently filled and the concave face of the bag, when distended by the water contents, is applied to the face or other part of the anatomy, a continuous annular bag zone to which the hot water is directly applied will be provided, for direct contact with the person. This zone may comprise the entire concave surface of the bag, if the bag is full, or only the lower portion of such concave surface, as, for instance, the part including the curved circular bottom piece 5. When an ordinary water-bag with parallel or flat sides or oppositely bulging or protruding sides is employed, the contents of the bag if the latter is but partly filled can shift about in the bag so that no definite zone of the contacting surface is directly heated by the water.

By the use of the bag of my invention a predetermined directly heated zone may be brought into contact with the portion of the anatomy to be treated and thus a more effective and positive treatment assured.

The bag of my invention constitutes I believe a novel entity in that it provides an inverted cup-shaped device adapted to be rested upon or brought in contact with any desired portion of the anatomy, so as to fit over the same, where protuberant as in treating the face, breasts, knees or shoulders, or so as to press into and intimately overlie the surface to be treated, depending upon the degree to which the bag is filled, as in application over the abdominal cavity. It tends better to hold its position upon the person than does the ordinary unstable water-bag, and a much less amount of hot water contents is required than in the ordinary water-bag, due to the peculiar relative formation of the walls 1 and 2 and the resultant interspace, such walls being brought together and connected at the margins of the central aperture 3. At times the weight of a filled ordinary water-bag is oppressive to invalids, and by use of the water-bag of this invention a relatively greater heated surface may be directly applied to the part to be treated by the use of such improved water-bag of relatively smaller outside dimentions and containing less water. It will be particularly noted that no straps, flaps, or other attaching or holding devices, such as are provided with other attempted improvements in water-bags, are required in the use of this invention, the two main walls with the connecting wall or bottom piece 5, the walls being of different formations, producing a structure, which, as above stated, serves effectively to hold itself in place upon the person and economically, uninterruptedly and effectively treat a relatively larger expanse of anatomical surface. The central opening 3 is not alone useful as a breathing opening, but serves to accommodate portions of the anatomy at the sides of which direct application of water-bag surface is desired, so as to prevent unfavorable pressure or undesired thermal treatment. Thus, application of heat may be made to a bodily area surrounding a cut or bruise or incision which may itself be omitted from the heated zone. Of course, if desired, the concave or protuberant wall 1 may be directly applied to the surface to be treated, where such application is preferable or more advantageous.

It is manifest that many changes may be made with respect to conformation, shape, dimensions, and relative arrangement and interconnection and form of parts, members and features, in departing from the specific disclosures of the foregoing specification and the drawing, all within the spirit of the invention and a fair interpretation thereof.

Having thus disclosed my invention I claim and desire to secure by Letters Patent:—

1. A water-bag formed of flexible water-proof material throughout, and comprising an inner wall and an outer wall, said bag having an opening through said walls and around the edges of which said walls are joined and from which they diverge to the outer edges of the bag where they are connected, both of said walls being cupped and the outer wall being more extensive than the inner wall, and said walls jointly constituting a concavo-convex figure.

2. A water-bag of circular form formed of flexible water-proof material throughout, and comprising an inner wall and an outer wall, said bag having a central opening therethrough, around the edges of which said walls are joined and from which they diverge to the outer edges of the bag where they are connected, both of said walls being formed upon segments of spheres but the outer wall being formed upon the segment of a sphere of greater radius than the inner wall, and said outer wall being eccentric to said inner wall whereby the bag as a whole is caused to maintain a concavo-convex formation throughout its area.

In witness whereof, I have signed my name to this specification in the presence of two subscribing witnesses.

ROBERT B. WHITMARSH.

Witnesses:

RAYMOND IVES BLAKESLEE,
FRANCIS L. ISGRIGG.